(12) United States Patent
Hartman et al.

(10) Patent No.: US 10,159,851 B2
(45) Date of Patent: *Dec. 25, 2018

(54) SYSTEMS AND METHODS FOR AUTOMATIC TRAINING OF DOSE PREDICTION MODELS AND TREATMENT PLANS AS A CLOUD SERVICE

(71) Applicant: Varian Medical Systems International AG, Cham (CH)

(72) Inventors: Joona Hartman, Espoo (FI); Maria Cordero Marcos, Vantaa (FI); Esa Kuusela, Espoo (FI); Jarkko Peltola, Tuusula (FI); Janne Nord, Espoo (FI)

(73) Assignee: Varian Medical Systems International SG, Cham (CH)

( * ) Notice: Subject to any disclaimer, the term of this patent is extended or adjusted under 35 U.S.C. 154(b) by 195 days.

This patent is subject to a terminal disclaimer.

(21) Appl. No.: 15/202,358

(22) Filed: Jul. 5, 2016

(65) Prior Publication Data

US 2016/0331999 A1    Nov. 17, 2016

Related U.S. Application Data

(63) Continuation of application No. 14/040,618, filed on Sep. 27, 2013, now Pat. No. 9,409,039.

(Continued)

(51) Int. Cl.
*A61N 5/10* (2006.01)
*G06F 19/00* (2018.01)

(52) U.S. Cl.
CPC .......... *A61N 5/1031* (2013.01); *A61N 5/103* (2013.01); *A61N 5/1043* (2013.01);

(Continued)

(58) Field of Classification Search
CPC combination set(s) only.
See application file for complete search history.

(56) References Cited

U.S. PATENT DOCUMENTS

| | | |
|---|---|---|
| 7,894,574 B1 | 2/2011 | Nord et al. |
| 7,986,768 B2 | 7/2011 | Nord et al. |

(Continued)

FOREIGN PATENT DOCUMENTS

| | | |
|---|---|---|
| EP | 2574374 | 4/2013 |

OTHER PUBLICATIONS

International Journal of Radiation Oncology Biology Physics vol. 97, Issue 1, Jan. 1, 2017, pp. 164-172 Highly Efficient Training, Refinement, and Validation of a Knowledge-based Planning Quality-Control System for Radiation Therapy Clinical Trials Nan Li PhD, et al. Elsevier.*

(Continued)

Primary Examiner — Michael B Holmes (57) ABSTRACT

The present invention proposes a method for automatically training a dose prediction model based on existing clinical knowledge that is accumulated from multiple sources without collaborators establishing communication links between each other. According to embodiments of the claimed subject matter, clinics can collaborate in creating a dose prediction model by submitting their treatment plans into a remote computer system (such as a cloud-based system) which aggregates information from various collaborators and produces a model that captures clinical information from all submitted treatment plans, and can be used to predict dose distributions (and other dose parameters) in subsequent treatment plans.

40 Claims, 4 Drawing Sheets

Related U.S. Application Data (60) Provisional application No. 61/798,852, filed on May 21, 2013.

(52) U.S. Cl.
CPC ...... G06F 19/3418 (2013.01); G06F 19/3481 (2013.01); *A61N 2005/1041* (2013.01); *A61N 2005/1074* (2013.01); *A61N 2005/1087* (2013.01)

(56) References Cited

U.S. PATENT DOCUMENTS

| | | | |
|---|---|---|---|
| 8,009,802 B2 | 8/2011 | Nord et al. | |
| 8,032,308 B2* | 10/2011 | Yu | A61N 5/1031 702/19 |
| 8,078,554 B2* | 12/2011 | Fung | G06N 7/005 706/12 |
| 8,121,252 B2 | 2/2012 | Nord et al. | |
| 8,278,633 B2 | 10/2012 | Nord et al. | |
| 8,280,003 B2 | 10/2012 | Torsti et al. | |
| 8,284,897 B2 | 10/2012 | Nord et al. | |
| 8,295,436 B2 | 10/2012 | Nord et al. | |
| 8,363,785 B2 | 1/2013 | Nord et al. | |
| 8,411,819 B2 | 4/2013 | Nord | |
| 8,416,918 B2 | 4/2013 | Nord et al. | |
| 8,579,784 B2* | 11/2013 | Krishnan | A61N 5/103 600/1 |
| 8,588,369 B2 | 11/2013 | Van Heteren et al. | |
| 8,693,630 B2 | 4/2014 | Nord et al. | |
| 8,710,445 B2* | 4/2014 | Bert | A61N 5/1048 250/363.04 |
| 8,744,148 B2 | 6/2014 | Nord et al. | |
| 8,816,307 B2 | 8/2014 | Kuusela et al. | |
| 8,835,878 B2 | 9/2014 | Nord et al. | |
| 8,961,382 B2 | 2/2015 | Nord et al. | |
| 9,060,698 B2 | 6/2015 | Van Heteren et al. | |
| 9,138,598 B2 | 9/2015 | Nord et al. | |
| 9,381,376 B2* | 7/2016 | Toimela | A61N 5/103 |
| 9,387,345 B2* | 7/2016 | Nord | A61N 5/1031 |
| 9,409,039 B2* | 8/2016 | Hartman | A61N 5/1031 |
| 9,463,334 B2* | 10/2016 | Kuusela | A61N 5/103 |
| 9,731,147 B2* | 8/2017 | Nord | A61N 5/1038 |
| 9,827,445 B2* | 11/2017 | Cordero Marcos | A61N 5/1031 |
| 9,901,749 B2* | 2/2018 | Van Heteren | A61N 5/1031 |
| 9,907,979 B2* | 3/2018 | Nord | A61N 5/103 |
| 9,974,975 B2* | 5/2018 | Peltola | A61N 5/1031 |
| 2010/0233707 A1 | 9/2010 | Buckingham | |
| 2012/0014507 A1 | 1/2012 | Wu et al. | |
| 2014/0270053 A1 | 9/2014 | Larson | |

OTHER PUBLICATIONS

A GPU implementation of a track-repeating algorithm for proton radiotherapy dose calculations Pablo P Yepes, Dragan Mirkovic and Phillip J Taddei IOP Publishing Physics in Medicine and Biology Phys. Med. Biol. 55 (2010) 7107-7120 doi:10.1088/0031-9155/55/23/S11.*

Prediction of Hemodynamic Response to Epinephrine via Model-Based System Identification Bighamian, R.; Soleymani, S.; Reisner, A.T.; Seri, I; Jin-Oh Hahn Biomedical and Health Informatics, IEEE Journal of Year: 2016, vol. 20, Issue: 1 pp. 416-423, DOI: 10.1109/JBHI.2014.2371533 IEEE Journals & Magazines.

Dose of dialysis predicted by continuous measurement of dialysate urea concentration Cappello, A.; Tartarini, R.; Paolini, F.; Calzavara, P Engineering in Medicine and Biology Society, 1996. Bridging Disciplines for Biomedicine. Proceedings of the 18th Annual International Conference of the IEEE Year: 1996, vol. 5 pp. 1813-1815 vol. 5.

The Lyman and a current parallel model: are they equivalent in predicting radiation induced lung toxicity Yorke, E.; Jackson, A.; Rosenzweig, K.; Merrick, S.; Ling, C. Engineering in Medicine and Biology Society, 2000. Proceedings of the 22nd Annual International Conference of the IEEE Year: 2000, vol. 1 pp. 694-697 vol. 1.

Machine Learning for Modeling Dose-Related Organ-at-Risk Complications after Radiation Therapy H. H. Zhang; L. Shi; R. R. Meyer; W. D. D'Souza Machine Learning and Applications, 2009. ICMLA '09. International Conference on Year: 2009 pp. 457-462, DOI: 10.1109/ICMLA.2009.55 IEEE Conference Publications.

Experimental Characterization and Numerical Modeling of Tissue Electrical Conductivity during Pulsed Electric Field for Irreversible Electroporation Treatment Planning R. E. Neal II; P. A. Garcia; J. L. Robertson; R. V. Davalos IEEE Transactions on Biomedical Engineering 2012, vol. 59, Issue: 4 pp. 1076-1085, DOI: 10.1109/TBME.2012.2182994.

Computerised conformal radiation therapy—a critical process C. J. Moore Computing & Control Engineering Journal Year: 1995, vol. 6, Issue: 5 pp. 205-210, DOI: 10.1049/cce:19950501 IET Journals & Magazine.

Predictive modeling of tumors using RP A. Kamrani; M. Azimi; E. A. Nasr Industrial Engineering and Operations Management (IEOM), 2015 International Conference on Year: 2015 pp. 1-8, DOI: 10.1109/IEOM.2015.7093789 IEEE Conference Publications.

* cited by examiner

Exemplary Computer System 400

Figure 4

SYSTEMS AND METHODS FOR AUTOMATIC TRAINING OF DOSE PREDICTION MODELS AND TREATMENT PLANS AS A CLOUD SERVICE

CLAIM OF PRIORITY

This application is a continuation of U.S. patent application Ser. No. 14/040,618, filed Sep. 27, 2013 to Hartman, et al., entitled "SYSTEMS AND METHODS FOR AUTOMATIC CREATION OF DOSE PREDICTION MODELS AND THERAPY TREATMENT PLANS AS A CLOUD SERVICE," now U.S. Pat. No. 9,409,039, which claims the benefit of U.S. Provisional Application No. 61/798,852, filed Mar. 13, 2013 also to Hartman, et al., and also entitled "SYSTEMS AND METHODS FOR AUTOMATIC CREATION OF DOSE PREDICTION MODELS AND THERAPY TREATMENT PLANS AS A CLOUD SERVICE," both of which are incorporated herein by reference in their entireties.

BACKGROUND OF THE INVENTION

Radiology is the branch of medical science dealing with medical imaging for the purpose of diagnosis and treatment. The practice of radiology often involves the usage of X-ray machines or other radiation devices to perform the diagnosis or administer the treatment. Other practices of radiology employ techniques that do not involve radiation, such as magnetic resonance imaging (MRI) and ultrasound. As a medical field, radiology can refer to two sub-fields, diagnostic radiology and therapeutic radiology.

Diagnostic radiology deals with the use of various imaging modalities to aid in the diagnosis of a disease or condition in a subject. Typically, a wide beam of X-rays at a relatively low dosage is generated from a radiation source and directed towards an imaging target. An imager positioned on the opposite side of the source with respect to the imaging target receives the incident radiation and an image is generated based on the received radiation. Newer technology and advanced techniques allow for improved image collection with the application of computerized tomography (CT) to medical imaging techniques. Conventional medical imaging processes involving CT scans typically produce a series of 2-dimensional images of a target area which can be subsequently combined using computerized algorithms to generate a 3-dimensional image or model of the target area.

Therapeutic radiology or radiation oncology involves the use of radiation to treat diseases such as cancer through the directed application of radiation to targeted areas. In radiation therapy, radiation is applied (typically as a beam) to one or more regions of the targeted area at pre-specified dosages. Since the radiation can be potentially harmful, extensive treatment planning may be conducted, sometimes far in advance of the actual treatment sessions, to pinpoint the exact location(s) to apply the beam, and to limit unnecessary exposure to the radiation to other areas in the subject. The treatment planning phase may include the performance of CT scanning or other medical imaging techniques to acquire image data that can be subsequently used to precisely calculate the proper position and orientation of the subject, location of one or more target areas within the subject, and to predict the dosage(s) of the radiation to be applied during therapy.

Traditionally, radiotherapy treatment plans are created by a human operator by manually defining optimization objectives to achieve a clinically acceptable plan. Recently, human operators can produce treatment plans automatically by utilizing existing clinical knowledge that is captured by an algorithm by using a training phase that requires the human operator to select examples for the algorithm.

Automatic planning by existing systems relies on the human operator to train the algorithm, which requires that the human operator has access to existing radiotherapy treatment plans. However, this may be prohibitive for clinics that are only starting to establish radiotherapy treatment. The problem is exacerbated since all of the data used to train an algorithm has to be accessible by the human operator responsible for training the algorithm and requires establishing communication links between all participants and knowledge bases. For beginning clinics and practices where such information is not available, automatic planning may not be an option at all.

Furthermore, once created, a treatment plan is often further optimized based on a variety of factors, such as the treatment condition, the patient, and available resources. However, optimizing a treatment plan manually is time consuming as the optimization objectives are iteratively changed and the resulting dose distribution may be repeatedly re-evaluated until an optimal plan is achieved.

A critical component of treatment planning is predicting the dosage and dose distribution of the radiation to be applied to the patient. In knowledge based dose prediction, information from previously planned radiation treatments are used to gain knowledge of what is an achievable dose distribution in a new case without performing the actual planning. One approach to knowledge based dose prediction is to use a set of the previously planned cases to create a prediction model that could then be used (without needing to store all information related to this training set) to predict the dose for a new case.

Typically, a prediction model contains information that is necessary to predict the dose distribution achieved for a given patient geometry if planning is performed according to techniques, objectives and trade-offs described by the model. These predictions can be transformed into optimization objectives that when used in combination with an optimization algorithm, produce a complete radiotherapy treatment plan. However, accumulating a library of treatment plans that covers a representative portion of patient variety in a single clinic may be difficult or impossible for certain treatment techniques due to their rarity. Transmitting patient sensitive data between multiple participants may be difficult due to local regulations.

Each model typically has certain regions where the model's predictions are valid; however, if geometric parameters of the new case differ too much from the geometric parameters planned by the training set, the dose predictions may no longer be reliable. In some instances, a clinic may have several models to cover a large variety of different regions. Sample treatment plans and models may also be shared between clinics, thereby increasing the number of available models even more. However, sharing individual models between multiple clinics results in clinics having possibly tens or hundreds of different, but possibly overlapping models. This may make clinical use of shared models tedious and inefficient.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

What is proposed is a method for automatically predicting a dose distribution based on existing clinical knowledge that is accumulated from multiple sources without collaborators establishing communication links between each other. According to embodiments of the claimed subject matter, clinics are able to collaborate in creating a dose prediction model by submitting their treatment plans into a remote computer system (such as a cloud-based system) which aggregates information from various collaborators and produces a model that captures clinical information from all submitted treatment plans, which can subsequently be accessed and used to predict dose distribution parameters in treatment plans for other patients or treatment subjects.

According to an aspect of the present invention, a system is provided that includes a first computing device equipped with a user input device operable to receive user input corresponding to a user selection of a selected dose prediction model (from a plurality of dose prediction models); and a processor operable to generate one or more optimization objectives based on the selected dose prediction model, and to predict at least one dose parameter based on the optimization objective. another aspect of the present invention, a method is proposed wherein a user can submit a patient geometry description into a software program residing on a remote computer system (later referred to as cloud service), which automatically generates and returns a radiotherapy treatment plan to the user based on a prediction model. According to such embodiments, a prediction model from a stored bank of prediction models is selected, based on geometrical characteristics of the patient case for example. A dose distribution is predicted based on the selected prediction model. Optimization objectives are then determined based on the predicted dose distribution and a treatment plan is generated based on the determined optimization objectives.

According to another aspect of the invention, a method and system is provided for training a dose prediction model by analyzing a training set of data to determine spatial information (of various organs and such), previously optimized treatment plans, and corresponding 3D dose distributions from multiple patents from the training set of data. The spatial information (implemented, for example, as one or more structure sets) can be converted into one or more data curves, with the geometric information being converted into organ specific distance-to-target histogram (DTH) curves. Additionally, a dose matrix can be converted into organ-specific dose-to-volume histogram (DVH) curves. These data curves can be further parameterized by determining the principal components of the curves, and a regression model can be determined and used to identify how DVH parameters can be predicted based on DTH parameters.

BRIEF DESCRIPTION OF THE DRAWINGS

The accompanying drawings are incorporated in and form a part of this specification. The drawings illustrate embodiments. Together with the description, the drawings serve to explain the principles of the embodiments.

DETAILED DESCRIPTION

Reference will now be made in detail to the preferred embodiments of the claimed subject matter, a method and system for the use of a radiographic system, examples of which are illustrated in the accompanying drawings. While the claimed subject matter will be described in conjunction with the preferred embodiments, it will be understood that they are not intended to limit these embodiments. On the contrary, the claimed subject matter is intended to cover alternatives, modifications and equivalents, which may be included within the spirit and scope as defined by the appended claims.

Furthermore, in the following detailed descriptions of embodiments of the claimed subject matter, numerous specific details are set forth in order to provide a thorough understanding of the claimed subject matter. However, it will be recognized by one of ordinary skill in the art that the claimed subject matter may be practiced without these specific details. In other instances, well known methods, procedures, components, and circuits have not been described in detail as not to obscure unnecessarily aspects of the claimed subject matter.

Some portions of the detailed descriptions which follow are presented in terms of procedures, steps, logic blocks, processing, and other symbolic representations of operations on data bits that can be performed on computer memory. These descriptions and representations are the means used by those skilled in the data processing arts to most effectively convey the substance of their work to others skilled in the art. A procedure, computer generated step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present claimed subject matter, discussions utilizing terms such as "storing," "creating," "protecting," "receiving," "encrypting," "decrypting," "destroying," or the like, refer to the action and processes of a computer system or integrated circuit, or similar electronic computing device, including an embedded system, that manipulates and transforms data represented as physical (electronic) quantities within the computer system's registers and memories into other data similarly represented as physical quantities within the computer system memories or registers or other such information storage, transmission or display devices.

Accordingly, embodiments of the claimed subject matter provide a method and system for automatic generation of treatment plans and dose prediction models on remote cloud computing components.

Configuring a DVH Estimation Model

Figure 1:
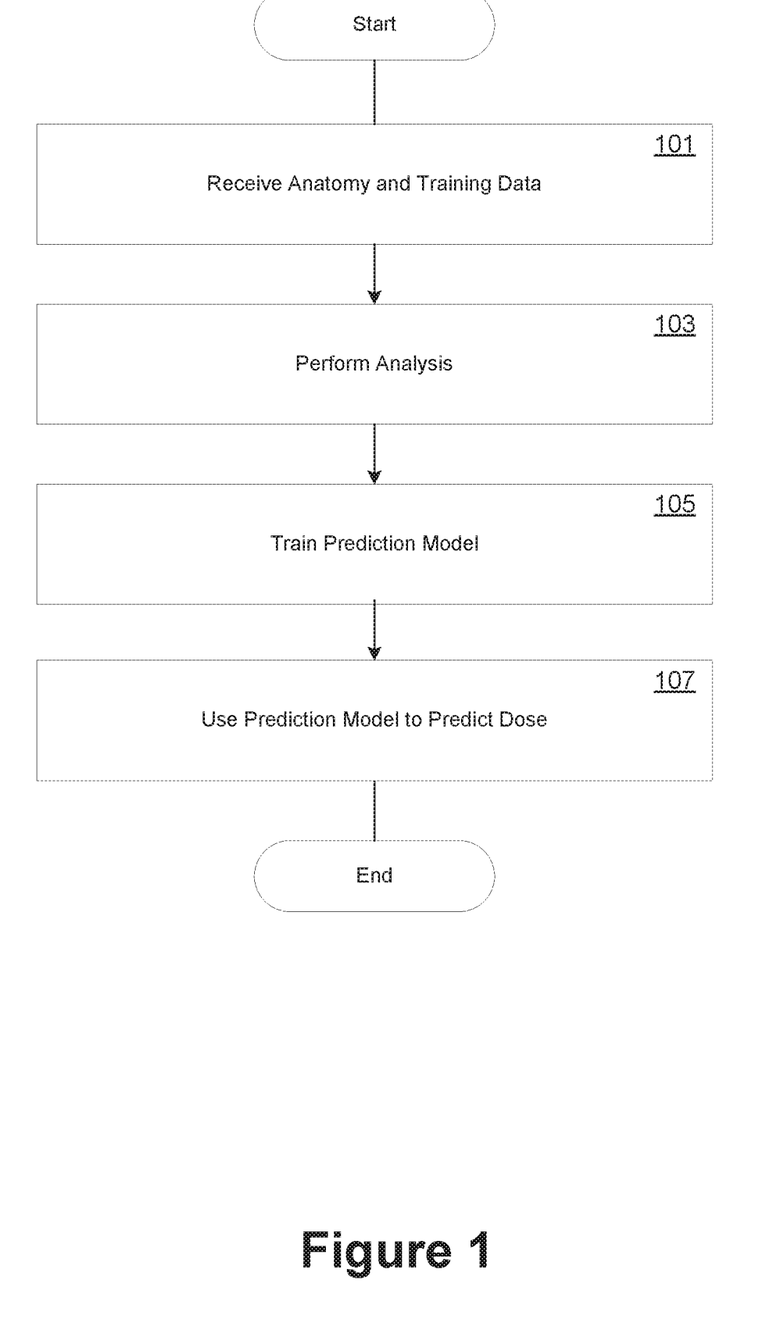
FIG. 1 depicts a flowchart of an exemplary process for selecting a training set of data for a dose prediction model, in accordance with various embodiments of the present invention.

FIG. 1 depicts a flowchart of a process 100 for configuring a dose prediction model. Steps 101 to 107 describe exemplary steps comprising the process 100 depicted in FIG. 1 in accordance with the various embodiments herein described. In one embodiment, the process 100 may be implemented in whole or in part as computer-executable instructions stored in a computer-readable medium and executed by a processor in a computing device.

According to one aspect, the dose prediction model may be used to predict dose parameters for a treatment plan corresponding to a radiation therapy patient. In one or more embodiments, the dose prediction model may be implemented as a dose-volume histogram (DVH) estimation model, where the predicted quantity is a dose volume histogram. In further embodiments, the prediction model may also generate a prediction based on a distance to target (DTH) histogram, which expresses the distance from a region or structure (such as an organ-at-risk) to a radiation target. In still further embodiments, the dose prediction model may be implemented as any other model suitable for predicting dosage (as a dose histogram, or spatial three dimensional dose distribution) for a radiotherapy treatment plan.

In one or more embodiments, a DVH estimation model can be configured by selecting a group of appropriate treatment plans from a treatment plan database (step 101). Ideally, the plans should be of high-quality, and sufficiently similar to a treatment being planned for a radiation target/patient, for example, in regard to the treatment area, field geometry, and fractionation. The system analyzes the patient anatomy (including, in some instances, anatomical information for each organ-at-risk (OAR)) and DVH values selected from this training set of plans (step 103), and trains a mathematical DVH estimation model (step 105) based on the patient anatomy and dose volume histogram values. Once trained, the prediction model may be used to predict (step 109) the dose parameters for the treatment plan of the radiation therapy patient. According to one or more embodiments, the process performs uniformity checks to the plans in a training set, and reports any significant deviations. When applying the model to a plan, the algorithm also checks whether the patient anatomy in the plan matches the training set.

DVH Estimation Model Training

Figure 2:
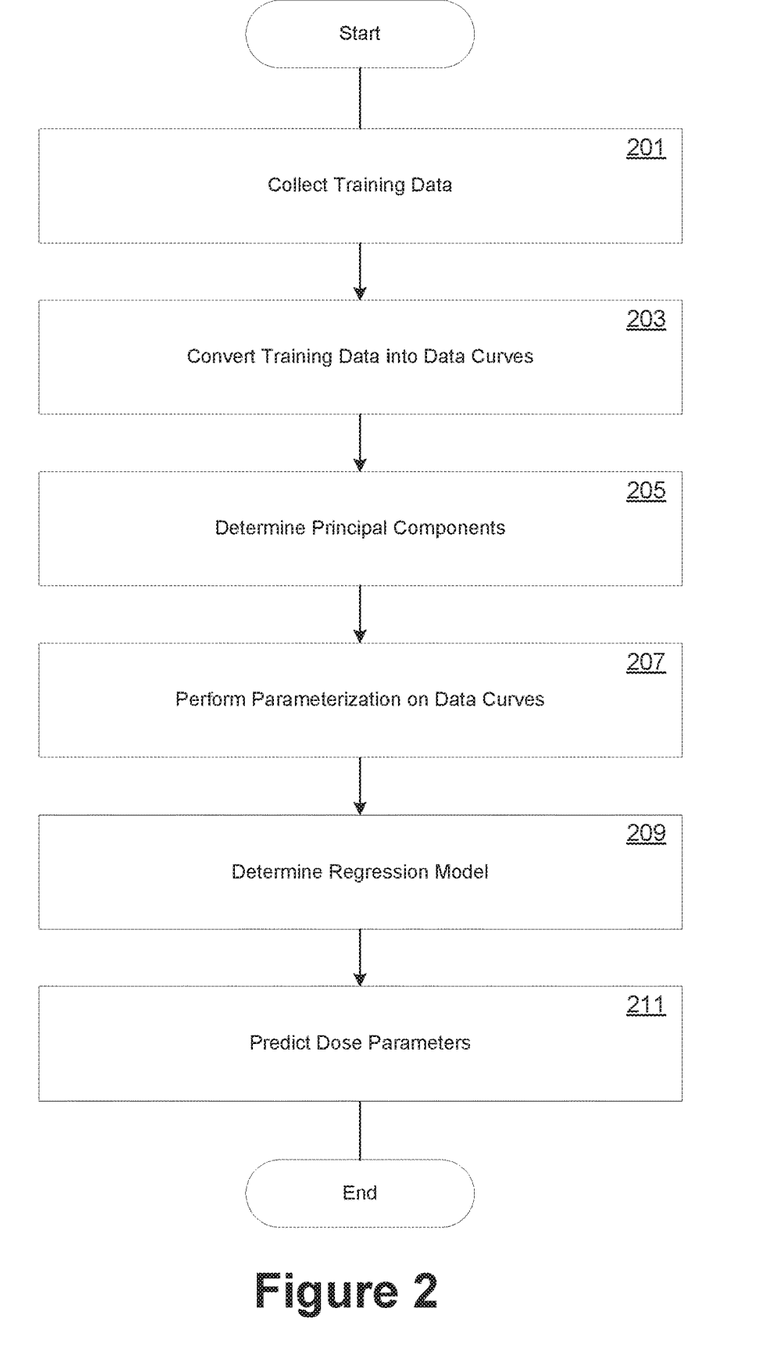
FIG. 2 depicts a flowchart of an exemplary process for training a dose prediction model, in accordance with various embodiments of the present invention.

Once the set of training data is selected, a prediction model may be trained (i.e., refined) to generate more precise dose estimations for the radiation therapy treatment being planned. FIG. 2 depicts the process 200 for training a prediction model. Steps 201 to 211 describe exemplary steps comprising the process 200 depicted in FIG. 2 in accordance with the various embodiments herein described. In one embodiment, the process 200 may be implemented in whole or in part as computer-executable instructions stored in a computer-readable medium and executed by a processor in a computing device.

In one or more embodiments, an implementation of a DVH estimation begins by analyzing the training set of data (selected at step 101) and parsing the data to collect structure sets (containing spatial information of various organs and the target), previously optimized treatment plans, and corresponding 3D dose distributions from multiple patients from the training set of data (step 201). In further embodiments, the estimation model may be used to convert (step 203) the structure sets into one or more data curves. For example, geometric information in a structure set can be converted into organ specific DTH curves. Likewise, a dose matrix may be converted into organ-specific DVH curves. These curves can be further parameterized (step 205) by first determining the principal components of the curves (e.g., structures) and the parameterization of the curves based on the determined principal components (step 207). Once parameterization is performed, a regression model can be determined (209) and used to identify how DVH parameters can be predicted based on DTH parameters (211). In one or more embodiments, a trained DVH model may include: 1) a list of treatment plans included in the model training set; 2) an identified plurality of principal components for a DVH and DTH for all organ at risk (OAR) structures in the model; 3) coefficients for a regression model; and 4) the mean and standard deviation for each anatomical feature in the training set.

According to various embodiments, parameterization of structures in a treatment plan may include generating a distance to target histogram (DTH). The parameter set related to each structure may include the principal components of a DTH; anatomical features, such as relative overlap volume, relative out-of-field volume, absolute OAR volume, and absolute target volume. According to further embodiments, a regression model may be generated as the relation between structure parameters and dose parameters in a training set. In still further embodiments, a separate regression model for each DVH principal component (e.g., each structure and dose) and for each OAR structure.

In one or more embodiments, in addition to creating DVH models, pre-constructed models within the system can be referenced for use in planning, validation, and optimization. In an embodiment, the models can be stored and shared within a clinic, or with other clinics. Sharing may be performed by hosting the stored data sets and/or constructed models in a network, such as a cloud infrastructure, accessible to remote users/clinics. By storing the data in cloud service infrastructures, data may be shared among a larger number of treatment planners and providers, without the need for each treatment center to acquire and maintain costly equipment. Moreover, each treatment center may control the amount and nature of the data shared, to preserve anonymity and confidentiality for their patients, for example.

Knowledge-Based Planning

Once constructed, a DVH Estimation model can be used as an aid in knowledge-based treatment planning. Knowledge-based treatment planning allows the application of knowledge derived from existing clinical patient cases to the treatment of new patients. The knowledge can be in the form of clinical protocols, templates, and model libraries (for contours and treatment plans). In particular DVH estimation models may be especially helpful by when creating new treatment plans and/or evaluating treatment plans.

In an embodiment, a treatment planning system includes a DVH Estimation tool, which uses the dose and patient anatomy information from existing plans to estimate the dose distribution in new plans. By using this tool, a user is able to generate optimization objectives and estimated DVH ranges for the structures (e.g., organs) in a treatment plan. The estimated DVH values may also be used as a starting point for treatment planners and provide assurances that a treatment plan is consistent with past experience. By applying the DVH Estimation solutions provided herein, a consistent level of quality can be maintained among treatment plans simply and effectively. The tool also reduces the number of optimization and evaluation iterations typically required during the generation of a treatment plan.

Figure 3:
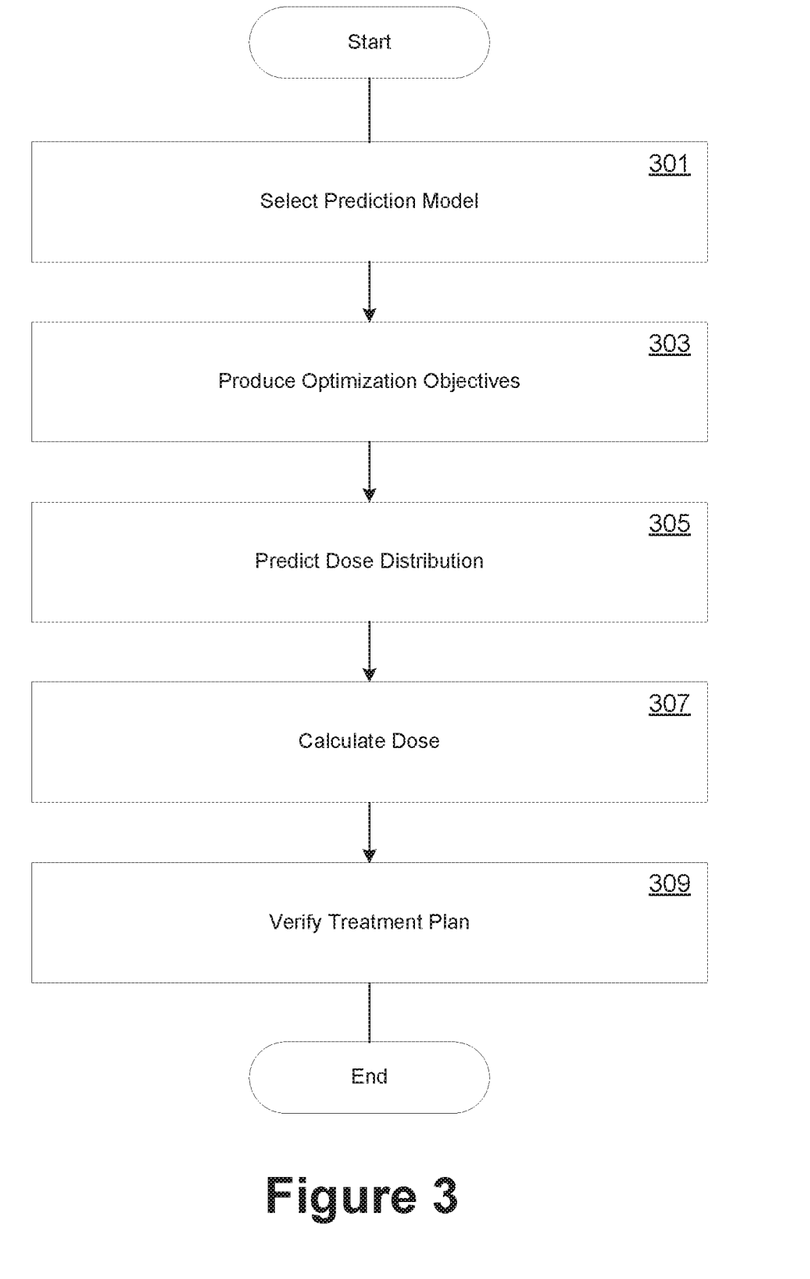
FIG. 3 depicts a flowchart of an exemplary process for automatically generating a treatment plan based on a dose prediction model.

FIG. 3 depicts a flowchart of a process 300 for automatically generating a treatment plan based on a prediction model. Steps 301 to 309 describe exemplary steps comprising the process 300 depicted in FIG. 3 in accordance with the various embodiments herein described. In one embodiment, the process 300 may be implemented in whole or in part as computer-executable instructions stored in a computer-readable medium and executed by a processor in a computing device.

In an embodiment, a prediction model is selected (step 301) from a library or storage base of pre-generated prediction models. The prediction model may, for example, comprise a DVH estimation model. Selection of the prediction model may be performed automatically, based on shared characteristics between the target of the treatment plan being generated and the treatment targets of treatment plans used to generate the selected prediction models. These characteristics may include, for example, a shared treatment type, target structure or regions, and set of organs-at-risk, etc. According to alternate embodiments, the user may also manually select the appropriate model for the planned treatment.

Once selected, the model(s) may be used to automatically create optimization objectives for a dose distribution (step 303), and automatically predict a dose distribution (step 305) for a treatment plan. In one embodiment, the dose distribution may be predicted as one or more estimated DVH ranges for the relevant anatomical structures involved in the treatment based on the predicted dose distribution. In one or more embodiments, the estimated DVHs are available for both the treatment plan (radiation) target, as well as the organs at risk (OAR). Calculation of the dose parameters may be subsequently refined in the current treatment plan in order to achieve the optimization objectives. Once the optimization is complete, a predicted dose can be calculated (step 307), after which the shapes and doses of the treatment plan may be compared (step 309) with the estimated DVH ranges for additional verification.

Automated Cloud Based Services

According to various embodiments, the processes of automatic creation of dose prediction models and automatic treatment planning may each (or both) be performed by a user remotely from the memory and processing centers (e.g., servers) performing the computations. In such embodiments, an authorized user of a computing device may access and manipulate the DVH modeling and stored treatment plan data via a network connection, e.g., the Internet. In further embodiments, the computing systems in which the data is processed and/or information (pre-constructed models, training set data, therapy plans) is stored may be implemented as cloud computing components. According to these embodiments, the computational resources required to host, maintain, and service the data and applications may be dynamically provisioned, and similarly reduced, as need and resource demands fluctuation with use.

According to an embodiment, a dose prediction model may be generated (as described above) by submitting treatment plans into a remote computer system, such as a server or virtual server of a cloud computing service. Once the data from various collaborators has been collected, the data is mined, and organized (according to various properties pertaining to patient condition, geometries, etc.). A model is then generated that captures the clinical information from all or a portion of the submitted treatment plans. According to further embodiments, patient confidentiality and anonymity may be preserved by extracting or condensing certain parameters, either prior to submission of the treatment plans, or via an automated data filtering process.

Once a dose prediction model is generated, the model may be used during an automatic treatment planning process. According to an embodiment, a treatment plan may be automatically generated with data hosted and/or processing performed on a remote computing device (such as a cloud server) by establishing a connection between the user and the cloud service provider. The user (if authorized) may then be prompted to select a prediction model from a composite storage base of pre-constructed prediction models. Selection may be based, at least partially, on characteristic similarities between the patient case and the prediction model, such as geometries, condition, etc.

Once the prediction model is selected, the dose distribution may be predicted, based on the selected model. Subsequently, optimization objectives based on the dose prediction may be produced, and a treatment plan based on the optimization objectives is then created.

Exemplary Computing System

Figure 4:
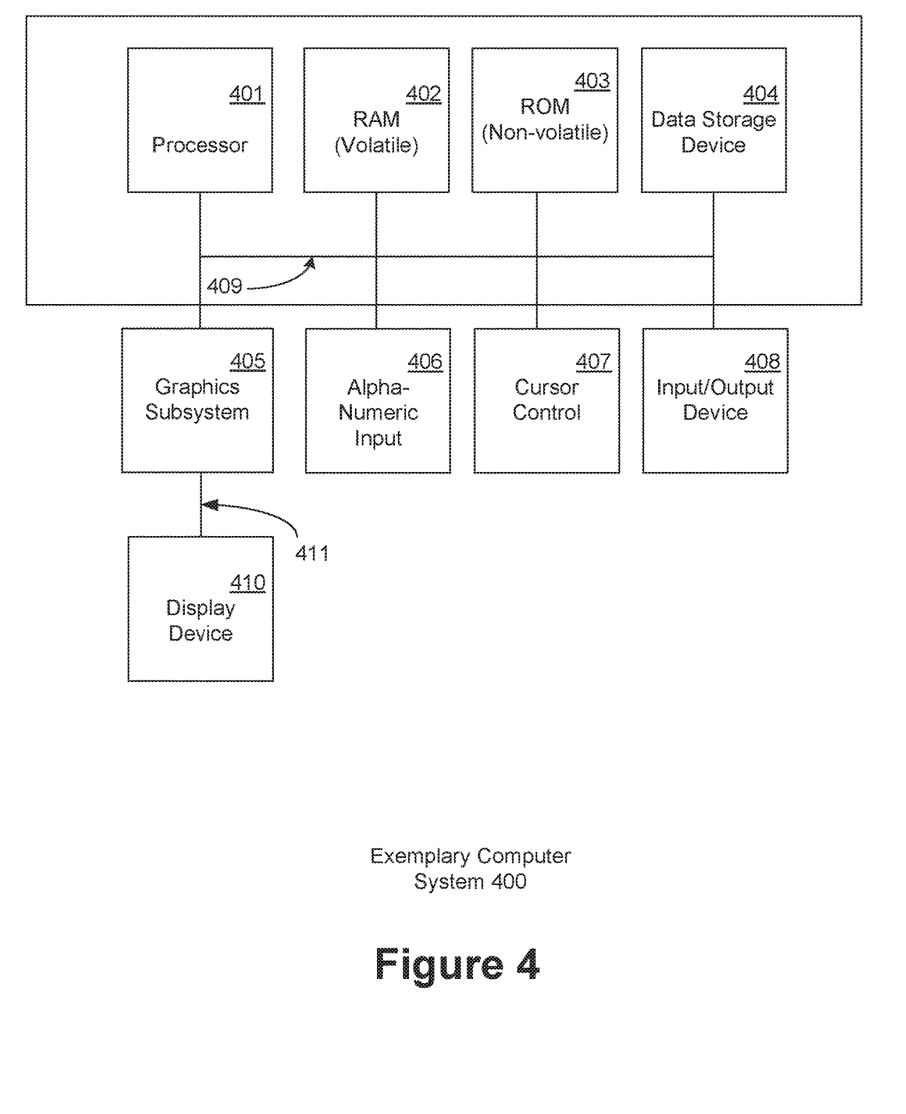
FIG. 4 depicts an exemplary computing environment, in accordance with embodiments of the present invention.

As presented in FIG. 4, an exemplary system 400 upon which embodiments of the present invention may be implemented includes a general purpose computing system environment, such as a computer operated by a remote user, or a server or virtual server of a cloud computing infrastructure. Imaging device 409, depicted in FIG. 4 and described above may, for example, be implemented as a computing system. In its most basic configuration, computing system 400 typically includes at least one processing unit 401 and memory, and an address/data bus 409 (or other interface) for communicating information. Depending on the exact configuration and type of computing system environment, memory may be volatile (such as RAM 402), non-volatile (such as ROM 403, flash memory, etc.) or some combination of the two.

Computer system 400 may also comprise an optional graphics subsystem 405 for presenting information to the computer user, e.g., by displaying information on an attached display device 410, connected by a video cable 411. According to embodiments of the present claimed invention, the graphics subsystem 405 may be coupled directly to the display device 410 through the video cable 411. A graphical user interface of an application for displaying images generated by a medical imaging device described above with respect to FIG. 1, and executing in the computer system 400 may be generated in the graphics subsystem 405, for example, and displayed to the user in the display device 410. In alternate embodiments, display device 410 may be integrated into the computing system (e.g., a laptop or netbook display panel) and will not require a video cable 411.

Additionally, computing system 400 may also have additional features/functionality. For example, computing system 400 may also include additional storage (removable and/or non-removable) including, but not limited to, magnetic or optical disks or tape. Such additional storage is illustrated in FIG. 4 by data storage device 407. Computer storage media includes volatile and nonvolatile, removable and non-removable media implemented in any method or technology for storage of information such as computer readable instructions, data structures, program modules or other data. RAM 402, ROM 403, and data storage device 407 are all examples of computer storage media.

Computer system 400 also comprises an optional alphanumeric input device 406, an optional cursor control or directing device 407, and one or more signal communication interfaces (input/output devices, e.g., a network interface card) 409. Optional alphanumeric input device 406 can communicate information and command selections to central processor 401. Optional cursor control or directing device 407 is coupled to bus 409 for communicating user input information and command selections to central processor 401. Signal communication interface (input/output device) 409, also coupled to bus 409, can be a serial port. Communication interface 409 may also include wireless communication mechanisms. Using communication interface 409, computer system 400 can be communicatively coupled to other computer systems over a communication network such as the Internet or an intranet (e.g., a local area network), or can receive data (e.g., a digital television signal).

In the foregoing specification, embodiments have been described with reference to numerous specific details that may vary from implementation to implementation. Thus, the sole and exclusive indicator of what is the invention, and is intended by the applicant to be the invention, is the set of claims that issue from this application, in the specific form in which such claims issue, including any subsequent correction. Hence, no limitation, element, property, feature, advantage, or attribute that is not expressly recited in a claim should limit the scope of such claim in any way. Accordingly, the specification and drawings are to be regarded in an illustrative rather than a restrictive sense.

What is claimed is:

1. A system for predicting a dose distribution, the system comprising:
 a first computing device comprising:
  a user input device operable to receive user input corresponding to a user selection of a selected dose prediction model from a plurality of dose prediction models; and
  a processor operable to generate at least one optimization objective based on the selected dose prediction model, and to predict at least one dose parameter for a radiation plan based on the at least one optimization objective,
 wherein the first computing device is comprised in a network of communicatively coupled computing devices.

2. The system according to claim 1, wherein the dose prediction model comprises a dose-volume histogram (DVH) estimation model comprising at least one DVH value, further wherein the at least one dose parameter comprises the at least one DVH value.

3. The system according to claim 2, wherein the processor is further operable to refine the at least one dose parameter based on the at least one optimization objective.

4. The system according to claim 1, wherein the at least one dose parameter comprises at least one DVH range for a plurality of anatomical structures corresponding to the radiation plan.

5. The system according to claim 4, wherein the plurality of anatomical structures comprises at least one of:
 a target of the radiation plan; and
 at least one organ at risk (OAR) incident to the target of the radiation plan.

6. The system according to claim 5, wherein the processor is further operable to perform an analysis of the radiation plan by: identifying at least one OAR comprised in the radiation plan, analyzing anatomical information for the at least one OAR, and modeling an effect on the at least one OAR based on the at least one DVH value.

7. The system according to claim 1, wherein the first computing device further comprises a memory device, the memory device being operable to store at least one of:
 a patient anatomy data corresponding to a target of the radiation plan;
 an absolute dose data corresponding to the target of the radiation plan;
 a structure set corresponding to the target of the radiation plan; and
 a set of training data.

8. The system according to claim 7, wherein the set of training data comprises at least one data set from the group consisting of:
 at least one structure set comprising spatial information of at least one OAR and a target of the radiation plan;
 at least one previously-optimized radiation plan; and
 a corresponding 3D dose distribution from at least one target of at least one previously-optimized treatment plans.

9. The system according to claim 1, wherein the dose prediction model corresponds to at least one pre-generated dose prediction model stored in a remote knowledge base, the knowledge base being comprised in a storage device of a second computing device accessible through a network to a plurality of computing devices comprising the first computing device.

10. The system according to claim 9, wherein the plurality of computing devices are disposed at a plurality of remotely distributed sites.

11. The system according to claim 10, wherein the at least one pre-generated dose prediction model comprises at least one DVH estimation model generated from at least one site of the plurality of remotely distributed sites.

12. The system according to claim 7, wherein the processor is further operable to train the dose prediction model by: analyzing the set of training data, converting the set of training data into a plurality of data curves, determining a plurality of principal components based on the plurality of data curves, performing a parameterization on the plurality of data curves, and determining a regression model for the plurality of data curves.

13. The system according to claim 12, wherein the processor is operable to predict the plurality of dose parameters based on the regression model.

14. The system according to claim 12, wherein the processor is further operable to convert the plurality of data curves by converting geometric information in the structure set into a plurality of organ-specific distance-to-target histogram curves.

15. The system according to claim 12, wherein the processor is further operable to convert the plurality of data curves by converting a plurality of dose matrices comprised in the structure set into a plurality of organ-specific dose-volume histogram curves.

16. The system according to claim 12, wherein the processor is further operable to train the dose prediction model by generating a trained dose prediction model from the dose prediction model, the trained dose prediction model comprising at least one of the data groups consisting of:
 a list of treatment plans comprised in the set of training of data;
 an identified plurality of principal components for a DVH and a distance to target histogram (DTH) for a plurality of OAR structures comprised in the dose prediction model;
 a plurality of coefficients for a regression model based on the trained dose prediction model; and a mean and standard deviation for a plurality of anatomical features comprised in the training set of data.

17. The system according to claim 16, wherein the processor is further operable to perform the parameterization on the plurality of data curves by generating a parameter set corresponding to a structure of the structure set, the parameter set being comprised from at least one the data groups consisting of:
 a plurality of principal components of the DTH;
 a relative overlap volume;
 a relative out-of-field volume;
 an absolute organ at risk volume; and
 an absolute target volume.

18. The system according to claim 1, further comprising a radiation therapy device configured to apply a radiation therapy beam having a dose parameter according to the radiation plan.

19. The system according to claim 18, wherein the radiation therapy device comprises a proton therapy device.

20. The system according to claim 18, wherein the radiation therapy device comprises a spot-scanning proton therapy device.

21. A method for training a dose prediction model, the method comprising:
 analyzing a training set of data to determine spatial information corresponding to a target of radiation treatment, at least one pre-stored treatment plan, and at least one dose distribution for the at least one pre-stored treatment plan;
 converting the spatial information into at least one data curve;
 parameterizing the at least one data curve;
 determining a regression model in response to the parameterizing; and
 identifying a prediction model for at least one dose distribution parameter based on the regression model.

22. The method according to claim 21, wherein the spatial information is comprised in at least one structure set corresponding to at least one of:
 the target of radiation treatment; and
 at least one organ at risk (OAR) proximate to the target of radiation treatment.

23. The method according to claim 21, wherein the at least one pre-stored treatment plan comprises at least one previously optimized treatment plan.

24. The method according to claim 21, wherein the at least one dose distribution comprises a three dimensional (3D) dose distribution from another target of radiation treatment.

25. The method according to claim 21, wherein converting the spatial information comprises using an estimation model to convert the spatial information into the at least one data curve.

26. The method according to claim 25, wherein the spatial information comprises geometric information, and wherein the at least one data curve comprises an organ specific distance to target histogram (DTH).

27. The method according to claim 21, wherein parameterizing the at least one data curve comprises determining at least one principal structure corresponding to the at least one data curve.

28. The method according to claim 27, wherein parameterizing the at least one data curve comprises generating a DTH and a parameter set for each principal structure corresponding to the at least one data curve.

29. The method according to claim 28, wherein the parameter set for a principal structure comprises at least one parameter from the group of parameters consisting of:
 an identification of principal components corresponding to the DTH; and
 at least one anatomical feature corresponding to the principal structure.

30. The method according to claim 29, wherein the at least one anatomical feature comprises at least one feature from the group of features consisting of:
 a relative overlap volume corresponding to the principal structure;
 a relative out-of-field volume corresponding to the principal structure;
 an absolute OAR volume corresponding to the principal structure; and
 an absolute target volume corresponding to the principal structure.

31. A system for training a plurality of dose prediction models, the system comprising:
 a shared library of treatment data, the library of treatment data comprising a plurality of pre-generated treatment plans;
 a first computing device comprising:
  a memory configured to store a patient anatomical data; and
  a processor configured to execute an application, the application being configured to analyze a training set of data comprised from the library of treatment data, to convert the training set of data into at least one data curve, to parameterize the at least one data curve, to determine a regression model based on the parameterization of the at least one data curve, and to identify a prediction model for at least one dose distribution parameter based on the regression model,
 wherein the shared library of treatment data comprises a cloud storage component communicatively coupled to a plurality of computing devices.

32. The system according to claim 31, wherein the processor is further configured to determine spatial information corresponding to a target of radiation treatment, wherein the spatial information is comprised in at least one structure set corresponding to at least one of:
 the target of radiation treatment; and
 at least one organ at risk (OAR) proximate to the target of radiation treatment.

33. The system according to claim 31, wherein a pre-generated treatment plan comprises at least one previously optimized treatment plan.

34. The system according to claim 31, wherein the at least one dose distribution parameter comprises a three dimensional (3D) dose distribution from another target of radiation treatment.

35. The system according to claim 32, wherein the processor is configured to convert the spatial information by using an estimation model to convert the spatial information into at the least one data curve.

36. The system according to claim 35, wherein the spatial information comprises geometric information, and wherein the at least one data curve comprises an organ specific distance to target histogram (DTH).

37. The system according to claim 31, wherein the processor is configured to parameterize the at least one data curve by determining at least one principal structure corresponding to the at least one data curve.

38. The system according to claim 37, wherein the processor is configured to parameterize the at least one data curve by generating a DTH and a parameter set for each principal structure corresponding to the at least one data curve.

39. The system according to claim 38, wherein the parameter set for a principal structure comprises at least one parameter from the group of parameters consisting of:
  an identification of principal components corresponding to the DTH; and
  at least one anatomical feature corresponding to the principal structure.

40. The system according to claim 39, wherein the at least one anatomical feature comprises at least one feature from the group of features consisting of:
  a relative overlap volume corresponding to the principal structure;
  a relative out-of-field volume corresponding to the principal structure;
  an absolute OAR volume corresponding to the principal structure; and
  an absolute target volume corresponding to the principal structure.

\* \* \* \* \*